United States Patent [19]

Sobieralski

[11] Patent Number: 4,783,536

[45] Date of Patent: Nov. 8, 1988

[54] SELECTIVE REDUCTION OF PENTACHLOROPYRIDINE TO 2,3,5,6-TETRACHLOROPYRIDINE WITH ZINC DUST IN BASIC MEDIA

[75] Inventor: Theodore J. Sobieralski, Antioch, Calif.

[73] Assignee: The Dow Chemical Company, Midland, Mich.

[21] Appl. No.: 699,273

[22] Filed: Feb. 7, 1985

[51] Int. Cl.$^4$ ............................................. C07D 213/61
[52] U.S. Cl. .................................................... 546/345
[58] Field of Search ......................... 546/345; 570/204

[56] References Cited

U.S. PATENT DOCUMENTS 3,993,654  11/1976  Dean et al. ........................... 546/345
4,111,938  9/1978  Redemann ............................ 546/345

FOREIGN PATENT DOCUMENTS 1499650  2/1978  United Kingdom ................. 546/345

Primary Examiner—Joseph Paul Brust
Attorney, Agent, or Firm—Robert R. Stringham

[57] ABSTRACT

The selective reduction of pentachloropyridine to 2,3,5,6-tetrachloropyridine is achieved by contacting the pentachloropyridine as a solution in perchloroethylene or methylene chloride with zinc dust in a basic aqueous medium.

10 Claims, No Drawings

SELECTIVE REDUCTION OF PENTACHLOROPYRIDINE TO 2,3,5,6-TETRACHLOROPYRIDINE WITH ZINC DUST IN BASIC MEDIA

BACKGROUND OF THE INVENTION

U.S. Pat. No. 4,111,938 is directed to the preparation of 2,3,5-trichloropyridine, an intermediate for the production of pesticides. The trichloropyridine is obtained by contacting a solution of pentachloropyridine (PCP) or 2,3,5,6-tetrachloropyridine (Sym-tet) in a water-immiscible solvent with zinc dust in the presence of an alkaline reagent having a pH of at least 11. The latter reagent preferably is aqueous NaOH.

Solvents named in the patent as being representative are benzene, toluene, xylene, ethyl benzene, hexane, heptane and anisole. The best yield (77% of theoretical) of the trichloro compound disclosed was obtained by refluxing at ~79° C. for five hours a mixture of 4 gram atoms of zinc dust and 1.25 liters of 8N aq. NaOH with a solution of 1 g. mole of PCP in 500 ml. of benzene. Substantially lower yields were obtained when the solvent was toluene or isopropanol. When 2-methoxyl-propanol was employed as the solvent, the yield of the trichloro compound was only 12% of theoretical.

No indication is given in the patent as to the relative rates of reduction of PCP and Sym-tet and it cannot be ascertained whether the disclosed method would be practical for the selective manufacture of 2,3,5,6-tetrachloropyridine.

Since the '938 patent issued (1978), Sym-tet has become an increasingly important intermediate for the production of the commercial insecticides DURSBAN* and LORSBAN* and the commercial herbicide GARLON* (*trademarks registered to The Dow Chemical Company). A variety of methods of preparing this intermediate have been devised, including the use of zinc dust in neutral or acidic media to reduce PCP dissolved in solvents such as acetic acid, isobutanol or dimethyl methylphosphonate. Two of these methods have been reported to give Sym-tet yields of up to about 91% of theoretical, but all of them leave something to be desired in one respect of another.

OBJECTS OF THE INVENTION

The primary object of the present invention is to provide a simple process by which Sym-tet can be selectively obtained from PCP in isolated yields as high as 95% of theoretical.

Another object is to avoid the aggravation of corrosion and operating pressure requirements attendant on the necessity for employing relatively high temperatures for prior art reductions in media which are low boiling and/or are poor solvents for PCP.

A further object is to provide a Sym-tet production method which does not require the use of phosphonate-type solvents for PCP.

Still other objects will be made apparent to those knowledgeable in the art by the following specifications and claims.

SUMMARY OF THE INVENTION

It has now been discovered that the foregoing objects can be attained by reduction of PCP with metallic zinc at temperatures up to about 55° C. in a basic aqueous media comprising a dispersion of the PCP in a liquid halocarbon having the essential character of perchloroethylene or, preferably, methylene chloride (dichloromethane).

The invention can be more narrowly defined as the method of producing 2,3,5,6-tetrachloropyridine which comprises stirring a mixture consisting essentially of zinc particles, water, a base and a solution of pentachloropyridine in a liquid chlorocarbon having the essential characteristics of perchloroethylene or, preferably, methylene chloride, the temperature of said mixture during said stirring being within the range of from about 20° to about 50° C., the duration of said stirring being about 6 hours or more, preferably about 10 hours, the relative amounts of said base and water being such as to be equivalent to aqueous NaOH of a concentration within the range of from about 5 to about 35 wt. %, preferably 30 wt. %, and the amount of said zinc charged to said mixture being from about 2 to about 4 gram atoms per gram mole of the pentachloropyridine.

The PCP present in the reaction mixture may be only partially dissolved in the halocarbon but any undissolved portion should be dispersed in the mixture in the form of droplets or fine particles.

By the term "equivalent" in the foregoing definition is meant that the concentration of hydroxyl ion in the aqueous phase is effectively the same as that in aqueous NaOH having a concentration within the specified range.

DETAILED DESCRIPTION

It has been found that the presence in the zinc of any substantial proportion of other metals—lead, most notably—is distinctly detrimental to the reduction. Accordingly, zinc having a purity at least equal to that of J. T. Baker reagent grade zinc powder is highly preferred. Though not considered indispensable, it is highly desirable that the zinc be as finely particulate as possible, short of being pyrophoric. Zinc metal commonly labeled as "dust" or "powder" is quite satisfactory.

The base used is preferably an alkali or alkaline earth hydroxide, NaOH being particularly preferred. However, strong organic bases such as tetramethyl guanidine, and choline, for example, may be suitable. The base which has actually been used is aqueous NaOH in concentrations up to 30 wt. %. Somewhat higher concentrations of NaOH, up to say about 35%, or even higher, may be operable; however, the likelihood of undesired C—Cl group hydrolyses will be correspondingly higher.

The amount of the base employed should be at least sufficient to provide two gram equivalents of hydroxyl ion per gram atom of zinc.

The degree of agitation of the reaction mixture should be at least sufficient to ensure good contact between the aqueous and organic phases. This may be achieved by means of a stirrer, a circulating pump or by vigorous refluxing. Preferably, the degree of agitation is such that the composition of any volume element of the mixture does not differ by more than a few percent from the average for the mixture as a whole.

The rate of reduction has been found faster when the solvent used is dichloromethane than when perchloroethylene is used. Both solvents are stable under the reaction conditions employed but dichloromethane has the further advantage of being lower boiling and thus is more readily removed in working up the reaction mixture. Other halocarbons have not been tried but are not ruled out. That is, any halocarbon which forms a liquid solution with PCP at a temperature of about 55° C. or less and does not react with the base, the zinc or hydrogen (produced by the reaction of zinc with water, particularly at temperatures of 55° or higher) to an intolerable extent may be said to have the characteristics essential to the practice of the present invention.

Preferably, the halocarbon is one in which PCP dissolves to the extent of at least 30 grams per 100 ml. of the solvent at the contemplated reaction temperature and is of a nature such that the solution of the sym-tet produced readily disengages from the aqueous phase.

At temperatures of from about 20° to 30° C., to attain essentially complete conversion of the PCP generally requires from 12 to 10 hours. At 50° C., reaction periods of 6 hours or less are generally sufficient. The progress of the reaction can readily be monitored by rapid analytical methods, such as IR or UV spectroscopy or vapor phase chromatography.

The reaction mixture may be worked up by known techniques. If the organic phase readily disengages, the mixture may be allowed to stand and the phases separated. The aqueous phase can be extracted with some fresh solvent and the extract combined with the organic phase. The resulting solution is then concentrated, chilled and filtered.

EXAMPLES

The following example is for purposes of illustration and is not to be construed as limiting the scope of the present invention in a manner inconsistent with the claims in this patent.

Example 1

A reaction mixture containing 3.3 grams (0.0131 g mole) of PCP, 3 grams (0.0459 g atom) of reagent grade zinc powder, 30 ml. of 30% aqueous NaOH and 30 ml. of methylene chloride was stirred for 10 hours at room temperature in a 100 ml. round-bottomed flask and then allowed to settle. The organic layer was separated and worked up in essentially the manner described above. 2.7 Grams (95% of theoretical yield) of a product identified as 2,3,5,6-tetrachloropyridine was obtained.

What is claimed is:

1. The process of preparing 2,3,5,6-tetrachloropyridine which comprises reducing pentachloropyridine with metallic zinc at a temperature of up to about 55° C. and in a basic aqueous medium comprising a dispersion of the pentachloropyridine in a liquid halocarbon having the essential character of perchloroethylene or methylene chloride.

2. The process of claim 1 in which said mixture consists essentially of zinc particles, water, a base and a solution of the pentachloropyridine and is stirred at a temperature of from about 20° to about 50° C. for a period of about 6 hours or more, the relative amounts of said base and water being such as to be equivalent to aqueous NaOH of a concentration within the range of from about 5 to about 35 wt. %, and the amount of said zinc charged to said mixture being from about 2 to about 4 gram atoms per gram mole of the pentachloropyridine.

3. The process of claim 1 in which said halocarbon is perchloroethylene or methylene chloride.

4. The process of claim 1 in which said halocarbon is methylene chloride.

5. The process of claim 2 in which said halocarbon is methylene chloride.

6. The process of claim 1 in which said base is an alkali or alkaline earth metal hydroxide.

7. The process of claim 2 in which said base is an alkali metal hydroxide.

8. The process of claim 2 in which said base is sodium hydroxide.

9. The process of claim 4 in which said base is sodium hydroxide.

10. The process of claim 5 in which said base is sodium hydroxide.

* * * * *